United States Patent [19]

Meller

[11] Patent Number: 4,776,794
[45] Date of Patent: Oct. 11, 1988

[54] CLEANING INSTRUMENT USING PREMIXED ABRASIVE LIQUID

[76] Inventor: Moshe Meller, 20 Rachel Street, Haifa, Israel, 34402

[21] Appl. No.: 870,178

[22] Filed: Jun. 3, 1986

[51] Int. Cl.$^4$ .............................................. A61K 5/00
[52] U.S. Cl. ...................................... 433/216; 433/88
[58] Field of Search .................. 433/84, 83, 88, 85, 433/125, 216; 51/427, 436, 438, 439

[56] References Cited

U.S. PATENT DOCUMENTS

| | | | |
|---|---|---|---|
| 2,441,441 | 9/1946 | Paasche | 51/8 |
| 2,814,877 | 7/1955 | Tilden | 433/88 |
| 2,825,135 | 1/1956 | Tilden | 433/88 |
| 2,874,470 | 5/1954 | Richards | 433/88 |
| 3,972,150 | 8/1976 | Hart | 51/439 |
| 4,090,334 | 5/1978 | Kurowski et al. | 51/427 |
| 4,097,995 | 7/1978 | Daune et al. | 433/125 |
| 4,174,571 | 11/1979 | Gallant | 433/216 |
| 4,184,258 | 1/1980 | Barrington et al. | 433/88 |
| 4,214,871 | 7/1980 | Arnold | 433/216 |
| 4,220,446 | 9/1980 | Walker | 433/85 |
| 4,236,889 | 12/1980 | Wright | 433/86 |
| 4,492,575 | 1/1985 | Mabile | 433/88 |
| 4,494,932 | 1/1985 | Rzewinski | 433/88 |
| 4,540,365 | 9/1985 | Nelson | 433/88 |
| 4,595,365 | 6/1986 | Edel et al. | 433/88 |
| 4,602,906 | 3/1984 | Gruenfelder et al. | 433/80 |
| 4,608,018 | 8/1986 | Ghedini et al. | 433/88 |
| 4,648,840 | 3/1987 | Conger, Sr. | 433/88 |
| 4,663,893 | 5/1987 | Savanick et al. | 51/439 |

FOREIGN PATENT DOCUMENTS 1174878 11/1981 Canada .............................. 433/125

OTHER PUBLICATIONS

Cavi-Endo, Dentsply/York. Division., #3607-D.
RMC Dental, DP32, Soluzioni Dentali.
EMDA, Dental Echo 2/86.

*Primary Examiner*—Robert Peshock
*Attorney, Agent, or Firm*—Frishauf, Holtz, Goodman & Woodward

[57] ABSTRACT

A cleaning device includes a source of a premixed abrasive liquid containing abrasive particles suspended therein. A nozzle head having a nozzle therein is coupled to a source of pressure air, whereby the nozzle accelerates or increases the velocity of the pressure air supplied thereto. The source of premixed asbrasive liquid is coupled to the nozzle head. In the nozzle head, the accelerated air is mixed with the premixed abrasive liquid and a jet of the mixture of accelerated air and abrasive liquid is provided at an outlet of the nozzle head, the jet being directed onto an object to be cleaned. The premixed abrasive liquid preferably comprises water, a plurality of abrasive particles suspended in the water, and a surface tension reducing agent for maintaining the abrasive particles in suspension. Liquids other than plain water can be used.

2 Claims, 4 Drawing Sheets

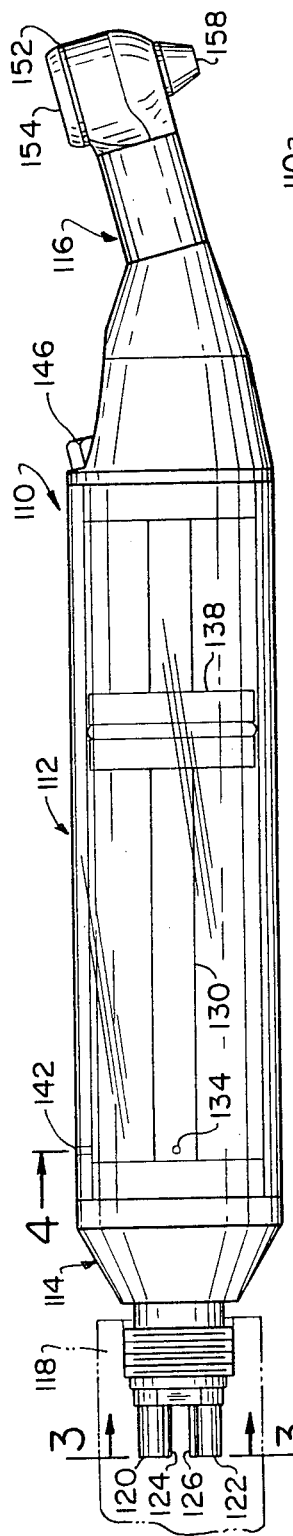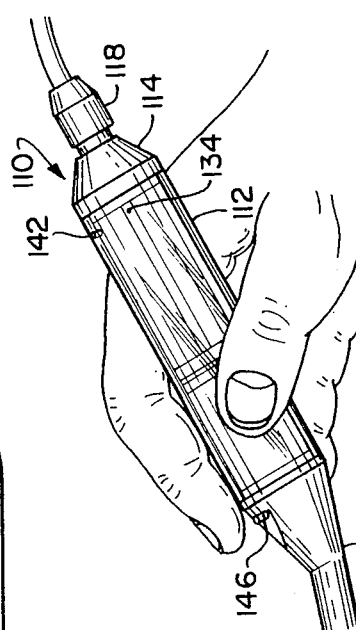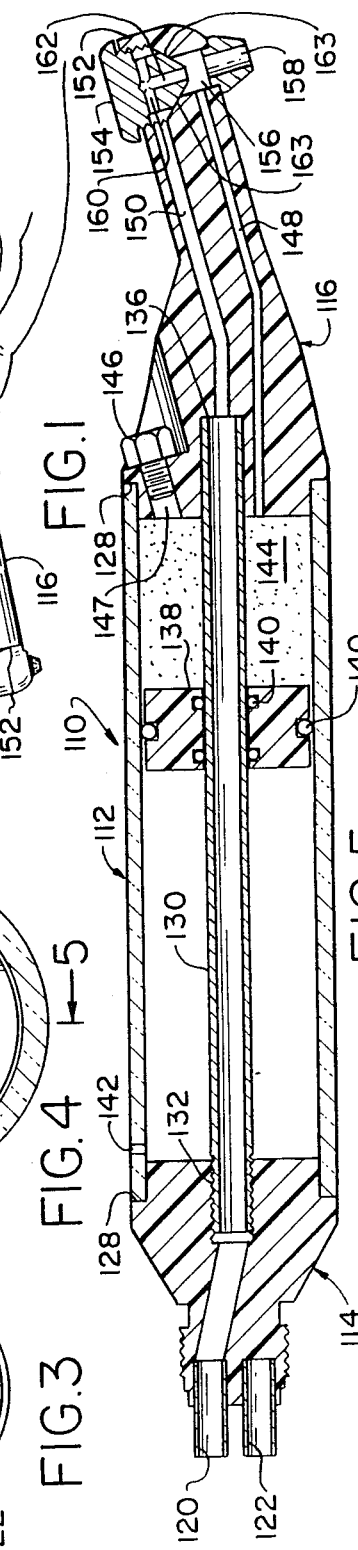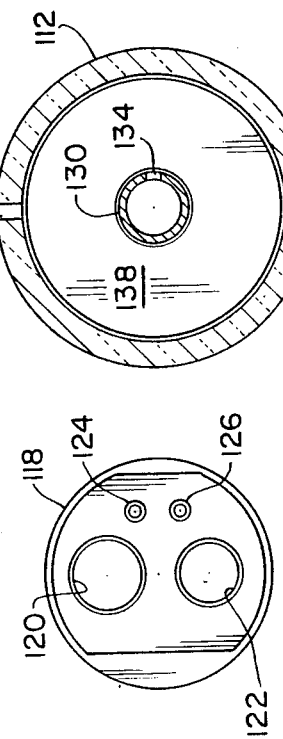

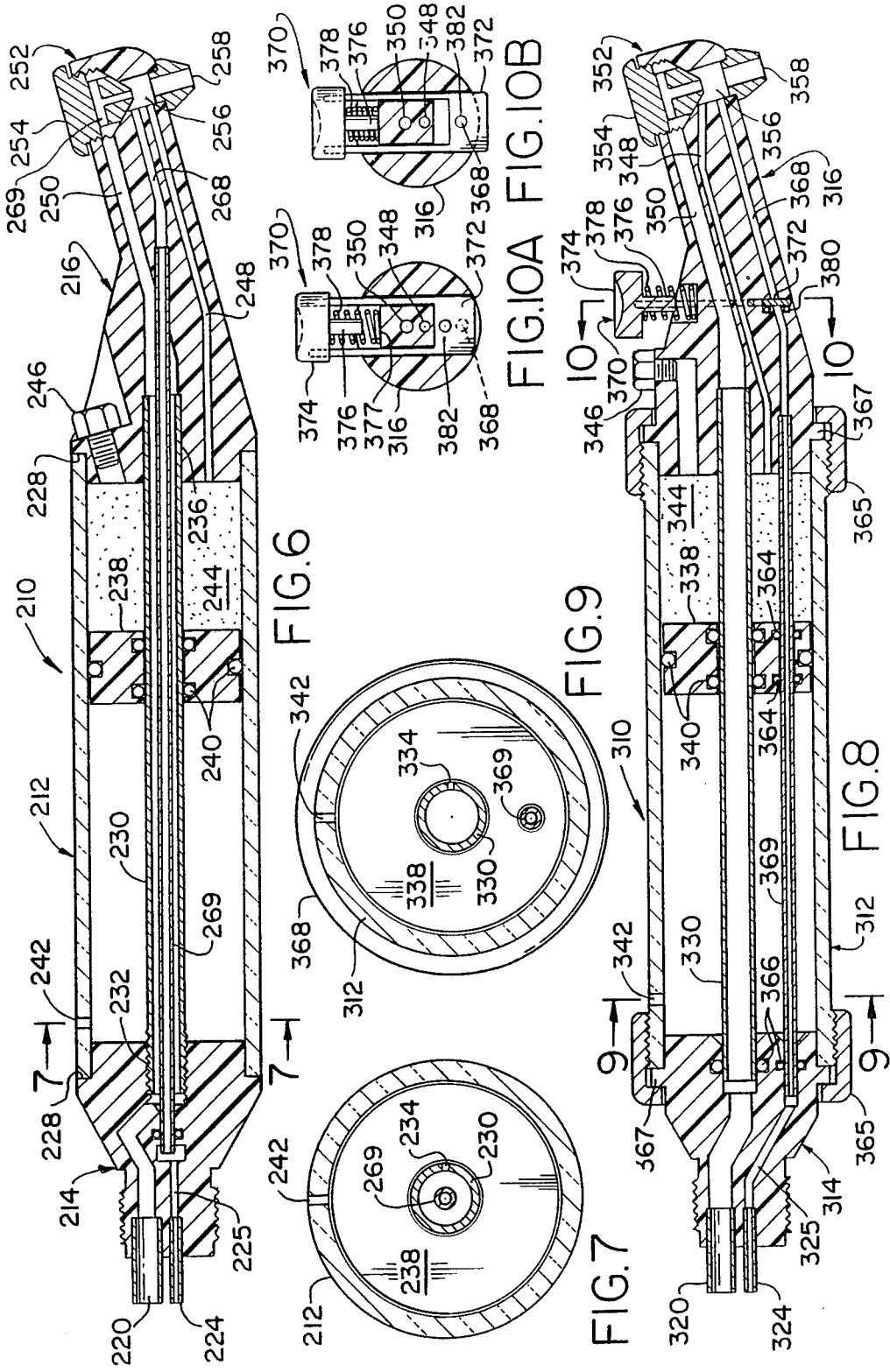

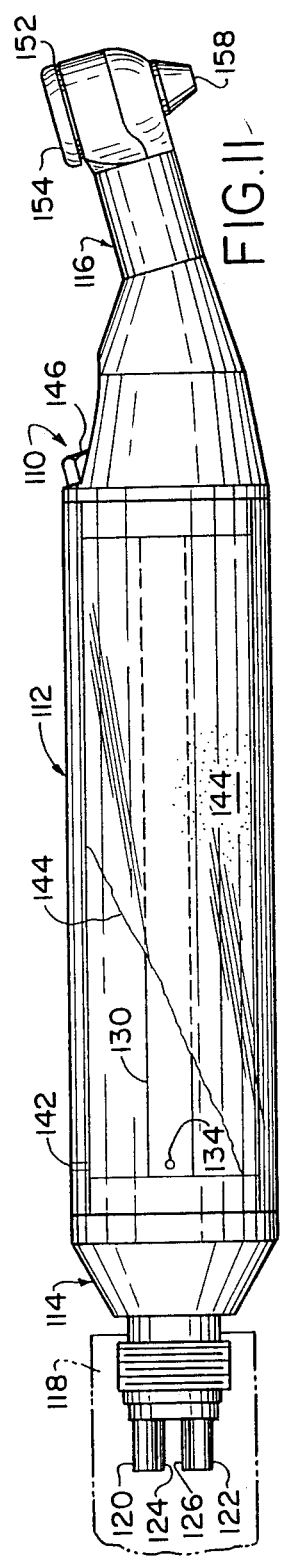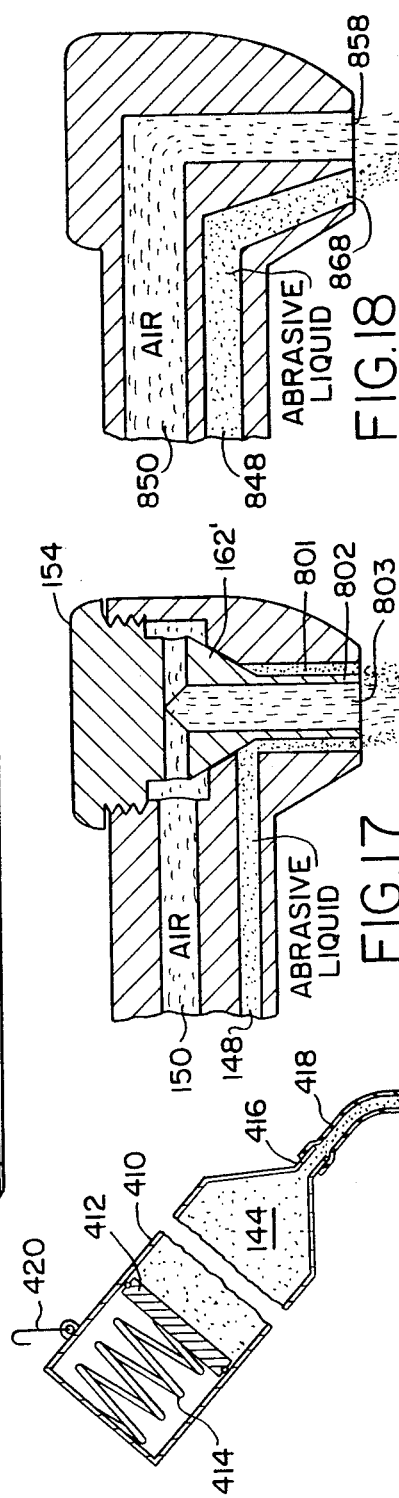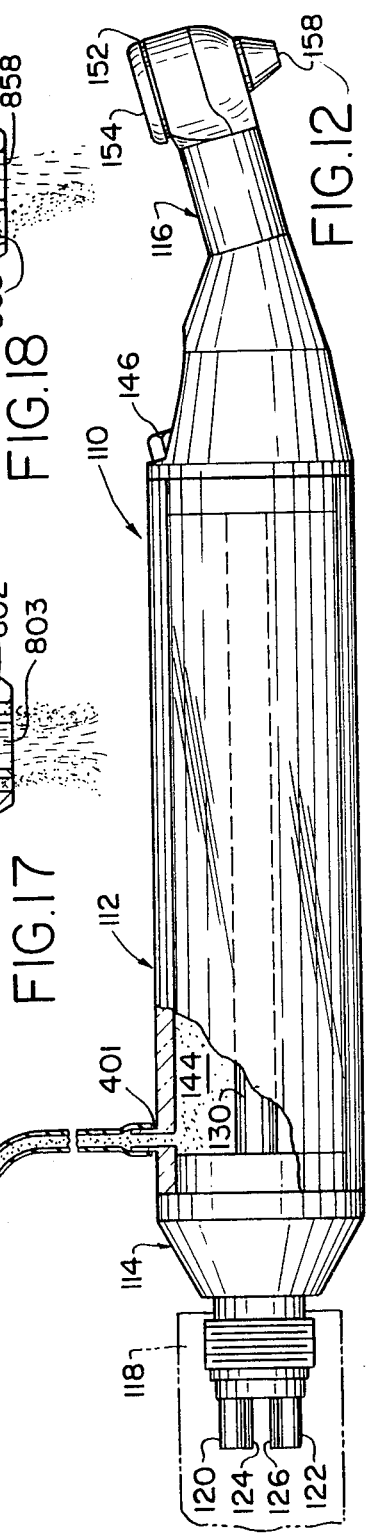

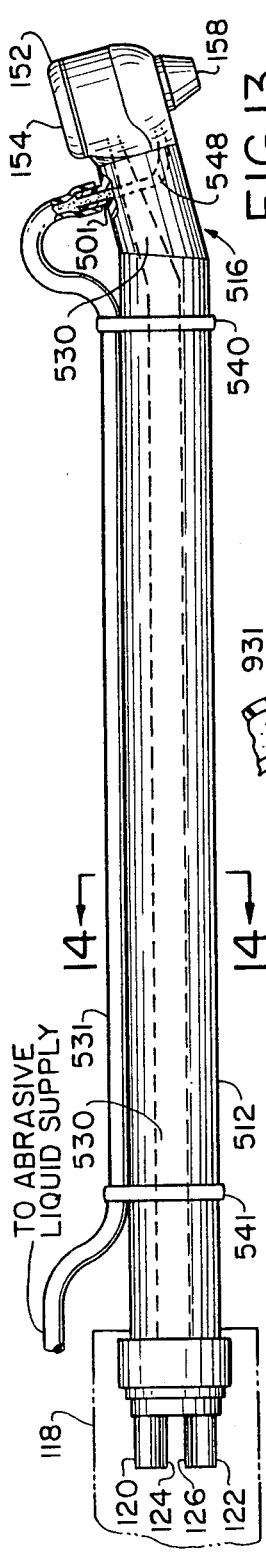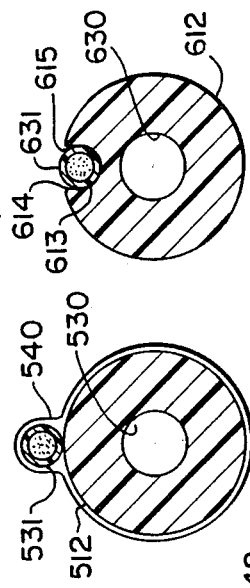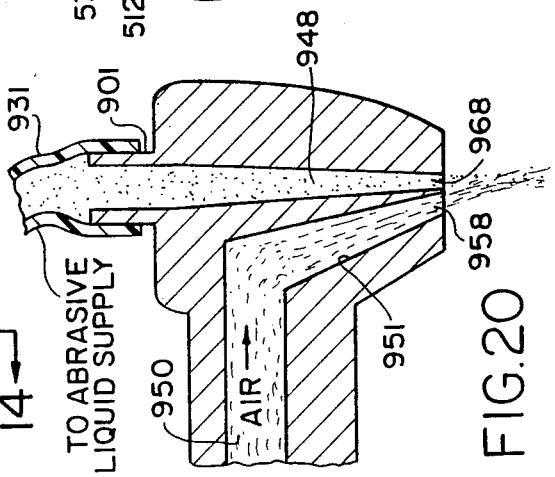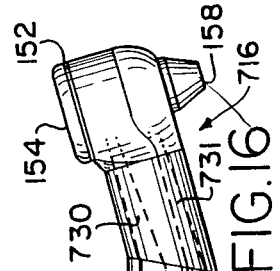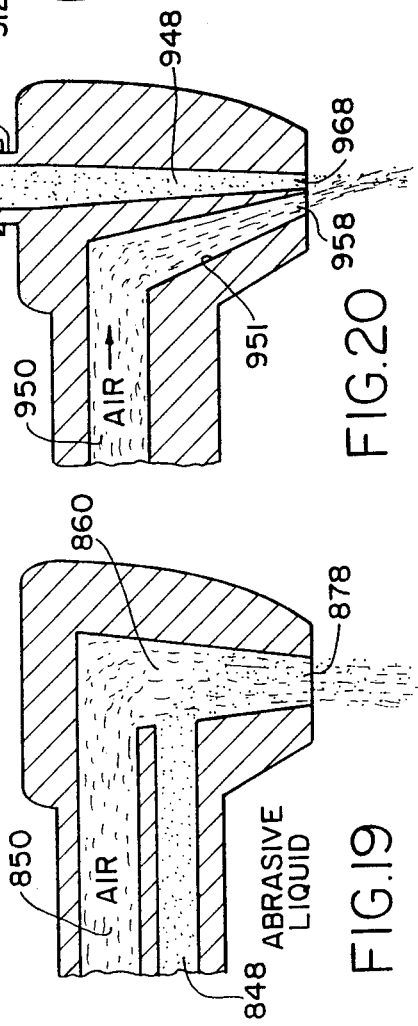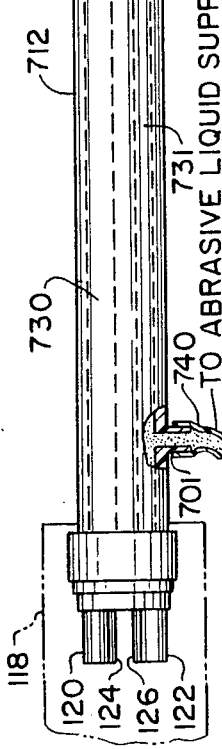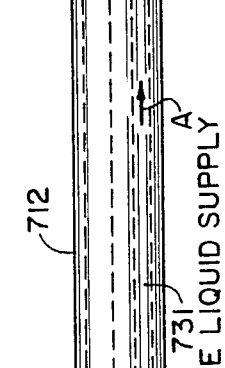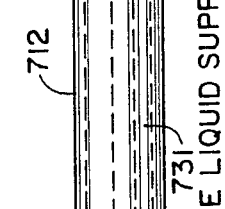

4,776,794

CLEANING INSTRUMENT USING PREMIXED ABRASIVE LIQUID

BACKGROUND OF THE INVENTION

This invention relates to a cleaning instrument using a premixed abrasive liquid (a liquid containing abrasive powder particles suspended therein), and more particularly to a dental cleaning instrument which dispenses a flow of air with the premixed abrasive liquid.

Various devices are known for cleaning teeth using a flow of air with powder particles therein. In some of these known devices, a flow of water (or other liquid) is combined with air and dry powder particles. The dry powder particles are mixed with the liquid and act as abrasive particles which clean the teeth when the liquid flow containing the powder particles is directed onto the surface of the teeth. The known devices are generally in the form of a hand piece which has a nozzle for directing a liquid jet, such as a water jet, containing the abrasive powder, onto the surface of the teeth to be cleaned.

The known devices use a supply of dry powder particles and have several difficulties and disadvantages. One such disadvantage is that in the known devices, the supply of dry powder particles (abrasive particles) tend to cake up in the instrument, thereby making cleaning extremely difficult. The "caking up" of the powder particles is a particular problem when the powder particles are exposed to high humidity conditions. In this case, clogging of the passages sometimes occurs. When the powder particles cake up or clog the device, it is extremely difficult to clean the instrument. In most cases, the instrument is not sufficiently dismantlable, so that cleaning becomes even more difficult.

Another disadvantage of the prior art is that it is very difficult to control the powder particle flow in the dry powder systems presently known in the art. That is, the powder flow becomes non-uniform, and the concentration of abrasive particles varies during use, and the volume of flow tends to vary during use. This is very disadvantageous since, when using the device to clean teeth, sensitive gum tissue may be damaged if the flow and concentration of powder particles is not accurately and uniformly controlled.

In some prior art devices, the dry powder container has been mounted separate from the hand piece in attempt to obtain easier and more accurate flow control. However, this arrangement still does not eliminate the caking up or clogging problem, and the flow of powder particles is still not as accurately controlable as desired.

The object of the present invention is to provide a dental cleaning apparatus for jetting a flow of air and powder particles onto the surface of teeth to be cleaned, in which caking up of the powder particles is not a problem, cleaning of the device is particularly easy and control of particle flow is accurately controllable. A further object of the invention is to provide such a device which is easily and quickly refillable. A still further object of the invention is to provide a compact relatively simple and inexpensive, dismantable, and easily cleaned apparatus having the foregoing advantages.

SUMMARY OF THE INVENTION

According to the present invention, a cleaning device uses a premixed abrasive liquid containing abrasive particles suspended therein, and comprises a housing; a nozzle head coupled to an end of said housing, and having a nozzle contained therein; a source of pressure air coupled to said nozzle head and to said nozzle, whereby said nozzle accelerates said pressure air; a source of a premixed abrasive liquid containing abrasive particles suspended therein; an outlet in said nozzle head in communication with said nozzle means for feeding said premixed abrasive liquid from said source to the vicinity of said outlet mean for accelerating and mixing with said pressure air; whereby said premixed abrasive liquid passes through said feeding means from said source and is jetted from said nozzle head outlet as a mixture with said pressure air. The premixed abrasive liquid comprises, in a dental embodiment, water, a biologically safe abrasive powder or particle component and a biologically safe surface tension reducing component (such as soap, detergent, toothpaste, etc.).

BRIEF DESCRIPTION OF THE DRAWINGS

FIG. 1 is a perspective view of a hand held dental cleaning device according to a first embodiment of the invention;

FIG. 2 is a side elevational view thereof;

FIG. 3 is a detail view of a standard dental tool coupling member, taken along line 3—3 in FIG. 2;

FIG. 4 is a cross sectional view of the device taken along line 4—4 in FIG. 2;

FIG. 5 is a cross sectional view of the device taken along line 5—5 in FIG. 4;

FIG. 6 is a schematic cross sectional view of a second embodiment of the invention;

FIG. 7 is a cross sectional view taken along line 7—7 in FIG. 6;

FIG. 8 is a longitudinal schematic cross sectional view of a third embodiment of the invention;

FIG. 9 is a cross sectional view taken along line 9—9 in FIG. 8;

FIG. 10 is a cross sectional view along line 10—10 in FIG. 8;

FIG. 10A shows a slide valve for use in the embodiment of FIG. 8, the slide valve being shown in its normally closed position;

FIG. 10B shows the slide valve of FIG. 10A in its depressed or open position;

FIG. 11 shows an embodiment similar to that of FIGS. 1-5, but without a piston 138;

FIG. 12 show another embodiment, similar to that of FIGS. 1-5, but using a separate container for the premixed abrasive liquid containing abrasive particles suspended therein;

FIG. 13 illustrates yet another embodiment of the invention using a separate container for the premixed abrasive liquid;

FIG. 14 is a cross-sectional view of the embodiment of FIG. 13 taken along the line 14—14 in FIG. 13;

FIG. 15 is a cross-sectional view, similar to that of FIG. 14, but of a modification to the embodiment of FIG. 13;

FIG. 16 shows still another embodiment using a separate container for the abrasive liquid;

FIGS. 17-19 illustrate modified nozzle head arrangements which are usable in all of the embodiments of the invention; and FIG. 20 illustrates a modified nozzle head arrangement when used with a separate container for the premixed abrasive liquid.

DETAILED DESCRIPTION

Various embodiments of the device of the present invention are shown in the drawings. Similar parts in each embodiment are designated by the same reference numerals, except for the hundreds prefix (that is, 100, 200 and 300), respectively for each of the several embodiments. While the specific devices are shown for dental use, the invention is useful in other applications, as will be apparent.

The hand held dental cleaning device 110 is generally shown in FIGS. 1 and 2. The device comprises an elongated cylindrical member 112, and input head end 114 at one end of the cylindrical member 112, and a nozzle end 116 at the opposite end of cylindrical member 112. FIG. 3 shows an end view of a common coupling arrangement 118 of a conventional dental system, wherein pipe 120 is the pressure air input line, pipe 122 is the air output line, pipe 124 is the water inlet line and pipe 126 is the water outlet. The device of the present invention is adapted to fit such a conventional dental coupling or arrangement 118. Conduits of the conventional coupling arrangement 118 which are not utilized in the present invention are merely dead ended in input head end 114 as the case may be, depending upon the particular embodiment. See, for example, pipe 122 in FIG. 5, which is show dead ended since it is not being used in the first embodiment of the invention.

As seen in FIG. 5, input head end 114 and nozzle end 116 both have similar shoulders 128 which bear against respective opposite ends of cylinder member 112. Air pipe or conduit 130 has one end thereof fixedly connected in the nozzle end 116 (by an adhesive threading or the like), and extends through the hollow cavity of cylindrical member 112. The left end of air pipe 130 is threaded at 132 and threadably engages mating threads in input head end 114. When the device is assembled, the input head end 114 is threaded onto the end of pipe 130 to cause the shoulders 128 to tightly bear against the opposite ends of cylindrical member 112, thereby providing an air tight and water tight seal. The pipe 130 serves as a tie rod to maintain the device together. A bleed hole 134 (see FIGS. 2 and 4) is provided in the pipe 130 near the input end 132 of pipe 130. The function of the bleed hole 134 will be discussed hereinbelow. Preferably, as shown in the drawings, pipe 130 extends through the center of the elongated housing for cylinder 112.

Concentrically and slidably located within elongated cylinder 112 and around pipe 130 is a piston 138 fitted with seal members 140 (preferably O-rings). The chamber defined to the right of piston 138 (see FIG. 5) is filled with a premixed abrasive liquid solution of dental cleaning material, such liquid having abrasive particles contained therein, preferably in suspension, and serving as abrasive particles for cleaning of tooth surfaces. The abrasive liquid is discussed in greater detail herein below. The chamber to the right of piston 138 is preferably filled with the premixed abrasive liquid (dental cleaning material) via a refill opening 147 which is selectively opened or closed via a threaded plug 146. Plug 146 is in the form of a screw having a hexagonal head which is engagable by a conventional tool for easy removal and installation. The chamber to the left of piston 138 is filled with air via the connector pipe 120, pipe 130 and bleed hole 134. The bleed hole 134 permits some of the input air to escape from the pipe 130 into the chamber to the left of piston 138 to pressurize the chamber to the left of piston 138.

During operation, pressure air flows freely through the input connector pipe 120, pipe 130 and air conduit passage 150 to nozzle head 162. The passage 150 is in communication with the downstream end of the pipe 130, as clearly seen in FIG. 5. The plug 154 is threadably inserted into the downstream end of the nozzle end 116, as shown in FIG. 5. The plug 154 has transverse passages 160 formed therein which communicate with an axial passage 162. The end surfaces 163 of plug 154 are inclined and bear against mating inclined surfaces at the end of nozzle end 116 in order to form an airtight seal. Thus, air from supply 120 flows through the transverse passages 160, through the longitudinal passage 162. The nozzle end 116 has a chamber 156 below the end of the plug 154, which chamber forms a Venturi chamber. Air rushing through passage 162 into the Venturi chamber 156 and out of the outlet passage 158 creates a suction effect in chamber 156 to draw abrasive liquid 144 from the chamber formed at the right hand side of piston 138, through the passage 148. The abrasive liquid 144 then enters the Venturi chamber 156 whereat it is mixed with the air flowing out of the passage 162. Since the piston 138 is pressurized at the left side thereof, it is therefor pushed to the right (as seen in FIG. 5), helping the abrasive liquid 144 to move through the passage 148 into the Venturi chamber 156. Because of the rapid air flow through the Venturi chamber 156, a negative pressure therein sucks the abrasive liquid 144 in combination with the positive pressure from the piston 138. A high velocity mix of air and abrasive liquid (containing abrasive particles) leaves the outlet 158 to be directed by the operator toward the target (tooth surface) to be cleaned.

As shown in FIG. 5, the left end of the cylindrical member 112 has an opening 142 therein. See also FIG. 1. If additional air pressure is required in the pressure chamber on the left side of the piston 138, the operator merely closes off the opening 142 (for example with a finger) to prevent flow of pressure air out of opening 142 and thereby increasing the positive pressure applied to the left side of piston 138.

The flow of air and abrasive liquid out of passage 158 can be controlled by controlling the air pressure applied through the inlet 120, for example with the conventional air supply control means used in dental equipment, which are often foot operated. If desired, a valve can be provided in passage 150 to adjust the air flow, as will be discussed further hereinbelow. In practice, it has been found that a control for the air flow in passage 150 is not required, since sufficient control of air flow can be provided by the remote pedal operated air supply which is conventionally used in dental equipment.

The device of FIGS. 1-5 is easily cleaned. The connector end 114 is unthreaded from the threaded end 132 of pipe 130 and is thereby easily removable therefrom. This releases the cylindrical housing 112 which is merely slipped off of the shoulder 128 of the nozzle end 116. The piston 138 can be easily removed by sliding same out of the cylindrical housing 112. The plug 154 is easily unthreaded from the remote end of the nozzle end 116. The individual parts are then easily cleaned, for example, in warm or hot water. Since a premixed abrasive liquid 144 is used, it is easily soluble in water and is easily cleaned out of the device, merely by the effect of the running water.

In order to refill the chamber with premixed abrasive liquid 144, during use, it is only necessary for the operator to block the outlet opening of passage 158, for example with a finger. Then, air pressure is applied through inlet 120, as in normal operation. Since the passage 158 is blocked off, air pressure builds up in chamber 156, which air pressure is communicated with the chamber to the right of piston 138 through the passage 148. Since the opening 142 in the housing 142 is open, the air pressure applied in this manner to the right side of piston 138 causes the piston 138 to move to the left as seen in FIG. 5. This operation takes less than one second. After the piston has moved to the left under the effect of this air pressure effect, the operator need only unblock passage 158, remove the screw plug 146, refill the chamber with premixed abrasive liquid 144, for example, from a squeeze bottle, and replace the screw plug 146 to re-seal the chamber containing the premixed abrasive liquid. Then, air pressure can be supplied at pipe 120 for resumption of operation.

FIGS. 6 and 7 illustrate a second embodiment of the invention. In this embodiment, air and water flow are controlled remotely, for example by means of foot pedal operated valves, or the like, as is conventional in dental equipment. As shown in FIG. 6, device 210 comprises a cylindrical member 212, and input head 214 and a nozzle end head 216. Since air inlet 220 and water inlet 224 are the only connections of concern in this embodiment, they are the only ones shown. In actuality, the other connections for water return and air return (used in conventional dental connectors) are dead ended in the input head end 214. As in the first embodiment, input air pipe 230 serves as a tie rod between input head end 214 and nozzle end 216. Air pipe 230 is fixedly mounted in the nozzle head end (as in the embodiment of FIGS. 1-5) and is threadably connected to the input head end 214 by threaded end 232. Piston 238 is fitted around air pipe 230 and operates in the same manner as piston 138 in the embodiment of FIGS. 1-5. Bleed holes 234 (in air pipe 230) and 242 (in cylindrical member 212) are as described in connection with the embodiment of FIGS. 1-5.

Should it be necessary or desirable to use a flow of water during the cleaning treatment, for example to make the premixed abrasive liquid 244 more fluid, or for diluting the premixed abrasive liquid 244 or for rinsing, a water pipe 269 is located concentrically within the air pipe 230. Water is then delivered to the water pipe 269 via the water inlet 224, water passage 225, and is delivered out of the water pipe 269 via water passage 268 in the nozzle head end which communicates the remote end of water pipe 269 with the Venturi chamber 256. Air is passed to the Venturi chamber in the same way as discussed in connection with FIGS. 1-5, through the air pipe 230, passage 250, and plug 254. A mixture of air, water and the premixed abrasive liquid (containing abrasive powder) then passes out of outlet 258 and is aimed at the target (tooth surface). In this embodiment, as mentioned above, air and water supply are controlled remotely. Flow of premixed abrasive liquid 244 is controlled as in the first embodiment of FIGS. 1-5. Refill of the device is accomplished in the same manner as in FIG. 5, by removal of the screw plug 246.

A third embodiment shown in FIG. 8 incorporates a separate water pipe 369 which is non-concentrically mounted between the input head end 314 and the nozzle end 316 within the cylindrical member 312. In this embodiment, since it is not possible to rotate the input end 314 relative to the cylindrical member 312, connecting nuts 365 were provided at the opposite ends to engage annular shoulders 367 which are respectively formed on the input end 314 and the nozzle end 316. Due to the tight coupling provided by the nuts 365, appropriate sealing is obtained between the ends of the cylindrical member 312 and the respective input end 314 and nozzle end 316, as in the other embodiments. Seals 366 are used at the input ends of pipes 330, 369 to prevent leakage of air at the connection with the input end 314. A similar seal is provided with respect to pipe 269 in FIG. 6. Additionally, seals 364 are provided to seal the piston 338 to the additional pipe 369. The seals 364, 366 are preferably elastic O-rings.

As in the foregoing embodiments, an air pressure bleed hole 334 is provided in pipe 330 (see FIG. 9), and a bleed hole 342 is provided in cylindrical member 312. These bleed holes function in the same manner as described with respect to the first two embodiments.

Water is supplied to the nozzle end 316 via water inlet 324, water passage 325, pipe 369 and water passage 368 in the nozzle end 316. Water passage 368 opens into the Venturi chamber 356, as in the embodiment of FIG. 6. Local control of the water flow in water passage 368 (in nozzle end 316) is provided by a gate valve 370. The gate valve 370, better seen in FIGS. 10A and 10B, comprises a slide 372 which rests against a seal 380 (for example an elastic O-ring) and maintains a blocked or non-flowing condition in the passage 368 as long as the operating button 374 is not pressed. When the button 374 is depressed by an operator for its full stroke against a biasing spring 378, the extention stop 376 bottoms on surface 377, at which point an opening 382 in the slide is in registration with the water passage 368 (see FIG. 10B). Water can then flow through the connector 324, pipe 369, valve 370, passage 368, chamber 356 and through the outlet 358. If the valve is depressed to a partially depressed condition, then only partial water flow is achieved, thereby permitting the operator to adjust the degree of water flow.

A similar valve could be provided to control air flow through passage 350. Moreover, a similar valve could be provided to control the flow of the premixed abrasive liquid or through the passage 348, but it is not contemplated that such a control would be required.

In the FIG. 8 embodiment, the arrangement and orientation of the refill threaded plug 346 is varied for convenience in the particular embodiment. Operation is identical with the arrangement shown in FIGS. 5 and 6.

In the embodiments of FIGS. 6 and 8, the piston can be moved to the left, after use, by using the same technique as described above with respect to FIGS. 1-5. That is, merely by blocking the outlet 258, 358 with a finger, the air pressure supplied through the air pressure supply line will feed back into the right-side chamber of housing 212, 312, to force the piston to the left. This operation takes less than one second to accomplish, and any water which is also fed back into the housing chamber is such a small quantity as not to interfere with operation. The small quantity of liquid which is fed back into the housing will not substantially dilute the premixed abrasive liquid (containing the particles) which is fed into the housing on the right side of the piston.

FIG. 11 shows a modified embodiment which eliminates the piston 138, 238, 338 in the embodiments of FIGS. 5, 6 and 8 respectively. The embodiment of FIG.

11 is substantially identical to the embodiment of FIG. 5, and the same reference numerals are used.

In the embodiment of FIG. 11, the gravity forces on the premixed abrasive liquid 144 when the device is held in operating position as shown in FIG. 1, in combination with the forces produced in the Venturi chamber 156 of the nozzle head end 116 are sufficient to jet the premixed abrasive liquid out of the nozzle head end with sufficient force and with sufficient controlability. Using this technique, approximately 80 percent of the premixed abrasive liquid in the housing 112 can be effectively used. If desired, the air bleed hole 134 in the air pipe 130 can be used to provide some air pressure within the housing 112. However, this opening 134 is preferably not provided since the additional air pressure may make it harder to control the flow of premixed abrasive liquid out of the nozzle head end. Therefore, in the embodiment of FIG. 11, it is preferred that the opening 134 be omitted. Additionally, if the opening 134 is omitted, the opening 142 should also preferably be omitted to prevent leakage of premixed abrasive liquid out of the housing 112.

FIG. 12 illustrates a further modified embodiment which is similar to that of FIG. 11 (without a piston in housing 112), but wherein a continuous feed of premixed abrasive liquid (containing abrasive powder particles suspended therein) is provided. As in FIG. 11, the embodiment of FIG. 12 is substantially identical to that of FIGS. 1–5, except for the elimination of the piston 138. Therefore, the same reference numerals are used throughout as applicable.

As shown in FIG. 12, the housing 112 further comprises a connection nipple 401 which opens into the cavity of the housing 112. In the embodiment of FIG. 12, the air pipe 130 does not have an opening 134 therein, and the housing 112 does not have an opening 142 therein. The apparatus further comprises a remote container 410 containing a premixed abrasive liquid 144 therein. Preferably, the remote container 410 includes a piston 412 which is spring biased by means of a spring 414 to apply a pressure on the premixed abrasive liquid 144 to force the premixed abrasive liquid 144 out of the mouth 416 of the container 410 and through the flexible conduit 418, the remote end of which is connected to the nipple 401. The remote container 410 also has a hook 420 to be hung from a fixture (not shown). Alternatively, the container may be fixedly mounted, remote from the hand held device 112, preferably at a level above the hand held device 112 so that gravity will aid in feeding the premixed abrasive liquid 144 into and through the cavity of housing 112. If the remote container 410 is mounted above the operating hand held unit, the piston 412 and biasing spring 414 can be eliminated. However, these elements are preferably provided to provide improved feed of the premixed abrasive liquid 144. After the remote container 410 is depleted or emptied, it can be removed from the hand held device merely by removing the conduit 418 from the nipple 401.

In the embodiment of FIG. 12, other pressurizing mechanisms for pressurizing the premixed abrasive liquid 144 in container 410 can be used, for example, air pressure, a pump-type pressurizing device, etc.

If desired, a valve could be provided on the air flow line the embodiments of FIGS. 11 and 12, similar to the valve of FIGS. 10a and 10b.

FIG. 13 illustrates another embodiment of the invention using a separate remote supply of premixed abrasive liquid. The separate supply of premixed abrasive liquid can be as shown in FIG. 12, or can be any other remote liquid source connected to the device by means of a flexible conduit 531. The supply of premixed abrasive liquid can be under pressure (for example as shown in FIG. 12), or the feeding pressure may be through gravity when the premixed abrasive liquid is mounted above the operating member of FIG. 13 or by the pressure differential at the outlet of the nozzle.

In FIG. 13, the housing 512 comprises a slender member having a bore 530 along the length thereof which is coupled to the air supply of connection head 118. The bore 530 extends completely through the length of the housing 512 and into the nozzle head 516 to communicate with, for example, the nozzle in the manner as shown in FIG. 5. In this connection, it is noted that the embodiment of FIG. 13 has the same nozzle and Venturi chamber arrangement as shown in FIG. 5. A separate flexible conduit 531 is provided to supply the abrasive liquid from a remote supply source. The conduit is clamped to the handle or housing 512 by means of clamps 540, 541 which may be split rings for easy installation over the housing 512 and conduit 531. The conduit 531 connects to a nipple 501 in the nozzle head 516, which is in communication with the Venturi chamber 156 via a passage 548 in the nozzle head 516. The passage 548 is displaced from the air passage 530 so as not to interfere with each other. In use, the device of FIG. 13 operates in substantially the same manner as that of the preceding embodiments, except that the abrasive liquid is supplied from a remote source and there is no reservoir in the housing or handle 512.

FIG. 15 illustrates a modified embodiment of the arrangement of FIG. 13 wherein the housing or handle 612 has an elongated recess 613 extending along the length threof and which accommodates the flexible conduit 631 (similar to the conduit 531 of FIG. 13). The conduit 631 leaves the elongated depression or opening 613 in the vicinity of the nozzle head (516 of FIG. 13) to connect to a nipple 501 as shown in FIG. 13. At the connector end 118 shown in FIG. 13, the conduit 631 leaves the elongated opening 613 to connect to a remote supply of abrasive liquid. The longitudinal edges 614, 615 of the elongated opening 613 are spaced apart a distance slightly less than the outer diameter of the conduit 631. Thus, the conduit 631 can be snapped into the opening 613 and is retained therein by the edges 614, 615, as shown in FIG. 15. In all other respects, the embodiment of FIG. 15 is identical to that of FIG. 13.

FIG. 16 illustrates yet another embodiment wherein the elongated housing or handle 712 has an elongated conduit 730 therein for carrying pressure air (as in FIGS. 13–15). The elongated housing further comprises another elongated conduit 731 for receiving abrasive liquid from a remote supply source. The elongated conduit 731 for abrasive liquid is deadended by the connector end 118 so that liquid flows only in the direction of the arrow A in FIG. 16. A nipple 701 is provided for connection of the conduit 740 to the conduit 731. Except for the fact that the conduit 731 is an internal bore in the housing 712, the embodiment of FIG. 16 is substantially identical to that of FIGS. 13–15 in operation. The nozzle used in this embodiment is substantially identical to the nozzle arrangement shown in FIG. 5.

In the embodiments of FIGS. 13–16, the abrasive liquid supplied to the device is accelerated in the nozzle head and is ejected from the outlet of the nozzle head in the form of a jet mixed with the pressure air. As in the previous embodiments, control valves could be provided to vary the flow of the pressure air and/or the abrasive liquid.

FIGS. 17-19 illustrate various modified nozzle heads which are usable in the various embodiments of the present invention. The nozzle head of FIG. 17 is very similar to that of FIG. 5 and the same reference numerals are used therein to identify substantially identical elements. In FIG. 17, the nozzle is substantially identical to the nozzle of FIG. 5, but the manner of mixing the abrasive liquid flowing in the conduit 148 is somewhat different. The arrangement of FIG. 17 comprises a substantially cylindrical space 801 around an elongated skirt-like member 802 which extends from the nozzle member 162'. An outlet 803 is provided for pressure air (which is accelerated in the nozzle). The accelerated air flowing out of the outlet 803 accelerates the abrasive liquid which is fed to the circular concentric chamber 801 via the conduit 148. This effect causes mixing and jetting of the abrasive liquid from the outlet, the resulting jet being used for cleaning, as in the previous embodiments.

FIG. 18 shows the pressure air being supplied to the nozzle head via conduit 850 and the abrasive liquid being supplied via conduit 848. The air is accelerated in the passage 850 and passes to the outlet 858. The conduit 848 terminates at an outlet 868 which is adjacent the air outlet 858. The air passing out of the outlet 858 creates a suction effect and draws the abrasive liquid from the outlet 868 so as to mix the abrasive liquid with the accelerated air in the form of an abrasive jet which is then used for cleaning.

FIG. 19 shows the abrasive liquid conduit terminating in the nozzle section 860, wherein the accelerated air from conduit 850 draws the abrasive liquid from the passage 848 so that a jet mixture of air and abrasive liquid exits from the exit 878 of the nozzle head.

The supply of abrasive liquid to the nozzle heads of FIGS. 17-19 may be as shown in FIGS. 1-12, or the supply may be from a remote source as shown in FIGS. 12-16. The particular orientation of the various conduits may be varied, as desired, to supply the appropriate substances to the conduits in FIGS. 17-19 as should be apparent.

FIG. 20 illustrates a further modified nozzle head which is useful with the housings or handles shown in, for example, FIGS. 13-15. In the embodiment of FIG. 20, the conduit 931 is connected to a source of abrasive liquid supply, for example as shown in FIG. 12. The conduit can run along the handle of FIG. 13 in the manner shown in FIG. 14 or in the manner shown in FIG. 15. Alternatively, the conduit 931 need not run along the handle member. The conduit 931 is connected via a nipple 901 to the nozzle head which is in communication with a passage 948 in the nozzle head which feeds the abrasive liquid to the outlet 968 of the nozzle head. Air is supplied via conduit 950 from, for example, a conduit extending through the handle or housing (for example the conduit 530 in FIG. 13), and through a restricted passage 951 which leads to an outlet 958. The air from conduit 950 is accelerated at the outlet 958 and combines with abrasive liquid from outlet 968 to form a jet mixture of high speed air and abrasive liquid, which jet is directed to the article to be cleaned. The high speed air exiting from outlet 958 draws the premixed abrasive liquid through the conduit 948 and out of the outlet 968. Even if no pressure is supplied on the liquid supply (as shown in FIG. 12), the effect of the high speed air leaving outlet 958 is sufficient to draw the abrasive liquid out of outlet 968 to provide the jet mixture which is used for cleaning. Alternatively, the conduit 931 can be coupled to a passage which leads to a Venturi chamber, such as Venturi chamber 156 of FIG. 5, whereat the air is mixed with the abrasive liquid.

Experiments have been conducted using the devices of the present invention for cleaning teeth. A suitable premixed abrasive liquid for such an application comprises about 40 percent water, about 40 percent abrasive particles and about 20 percent surface tension reducer, the percentages being by volume. The surface tension reducer can be soap, detergent, toothpaste or other known biologically safe surface tension reducers. The surface tension reducer helps keep the abrasive particles in suspension in the liquid to prevent settling thereof. For dental applications, the abrasive powder particles can be fine ground sodium bicarbonate (baking soda) or standard "prophy powder", generally used in the tooth cleaning art, for example the powder designated "Prophy Matic" distributed by Medidenta International, Inc., Woodside, N.Y. When sodium bicarbonate is used in the abrasive liquid for cleaning teeth, it has been found that a grain size for the sodium bicarbonate of from about 1 to 100 microns is suitable for providing satisfactory results. A narrower suitable range is from about two or three microns to about 50 microns, and more particularly from about 5 microns to about 15 microns. Other grain sizes could be used. A particularly suitable surface tension reducer has been found to be toothpastes, such as Crest toothpaste, Aim toothpaste, etc. Not only do these products provide suitable surface tension reduction to keep the sodium bicarbonate particles in suspension, but they also are proven biologically safe, and add a pleasant flavor to the abrasive liquid, thereby reducing patient discomfort during use. While approximately 40% water, 40% abrasive particles and 20% surface tension reducers, by volume, is a suitable premixed abrasive liquid, other percentages could be used. For example, the volume of water may be from about 10% to 90%, or from 30% to about 70% (40-60% preferred, and 40-50% being more preferable), with corresponding adjustments in the volume of the surface tension reducer and abrasive particles. The surface tension reducer can be from 0% to about 60 or 70%, with 10-30% being preferred and 15-25% being more preferable. The critical factor is that the resulting abrasive liquid should have sufficiently low viscosity to permit flowing thereof through the various passages and to be accelerated by the accelerated air flow. For other cleaning applications other known abrasive particles can be used.

It has been found that the device of the present invention can be used not only for cleaning articles such as teeth, but also for polishing. In the case of polishing, the premixed abrasive liquid constituents generally have the same volume percentages, but the abrasive powder (such as a "prophy powder") is replaced by a polishing powder, such as very finely ground baking soda powder.

Other powders, surface tension reducers and liquids (instead of water) could be used as desired, so long as the resulting abrasive liquid is of sufficiently low viscosity to permit flowing thereof through the passages leading from the housing 112, 212, 312, 512, 712 to the Venturi chambers 156, 256, 356, and out of the outlet members 158, 258, 358, respectively. When used in dental cleaning and polishing operations, all of the materials, must be biologically safe.

The device of the present invention is not limited for use in dental operations. It would be useful for other purposes such as for jewelry finishing or cleaning, cleaning items such as spark plugs, corroded articles, polishing steel or other metal injection molds, etc. Moreover, the geometry may be varied to enlarge the device for use in large cleaning operations which require a sand-blasting effect.

I claim:

1. A method of dental cleaning using a premixed abrasive liquid containing abrasive particles suspended therein, in combination with an elongated, hand grippable and hand holdable housing member having opposite end portions, a nozzle head being coupled to one of said opposite end portions of said housing member, said nozzle head having a nozzle contained therein, and said nozzle head having an outlet in communication with said nozzle, the method comprising:

coupling a source of pressure air to the other of said opposite end portions of said housing member;

coupling said pressure air from said pressure source to said nozzle head and to said nozzle, via a first conduit means in said housing member, whereby said nozzle accelerates or increases the velocity of said pressure air;

containing a predetermined quantity of a premixed abrasive dental cleaning liquid comprising a liquid with abrasive particles suspended therein in a containing means in said housing member;

maintaining said premixed abrasive liquid in said containing means under pressure by feeding some of said pressure air against a piston in said containing means, said piston applying pressure to said premixed abrasive liquid in said containing means;

supplying said pressurized premixed abrasive liquid from said containing means to said nozzle head via a second conduit means in said housing member;

mixing said pressurized premixed abrasive liquid with said accelerated pressure air in said nozzle head; and passing of said pressurized premixed abrasive liquid through said second conduit means from said containing means to said nozzle head and jetting said pressurized premixed abrasive liquid from said nozzle head outlet under the influence of substantially only the accelerated pressure air.

2. The method of claim 1, wherein said step of coupling said source of pressure air to said opposite end portion of said housing member comprises coupling a conventional dental supply tube to a connector which is mounted on said opposite end portion of said housing member.

* * * * *